(12) United States Patent
Dalton et al.

(10) Patent No.: US 9,161,198 B2
(45) Date of Patent: *Oct. 13, 2015

(54) SYSTEMS AND DEVICES FOR EMERGENCY TRACKING AND HEALTH MONITORING

(71) Applicant: ActiveCare, Inc., Orem, UT (US)

(72) Inventors: James Dalton, Orem, UT (US); Michael Acton, Jordan, UT (US); Peter Derrick, Farmington, UT (US)

(73) Assignee: ActiveCare, Inc., Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,644

(22) Filed: Jan. 26, 2015

(65) Prior Publication Data

US 2015/0208222 A1  Jul. 23, 2015

Related U.S. Application Data

(63) Continuation of application No. 12/614,242, filed on Nov. 6, 2009, now Pat. No. 8,942,676.

(51) Int. Cl.
| | |
|---|---|
| *H04W 4/22* | (2009.01) |
| *A61B 5/00* | (2006.01) |
| *A61B 5/145* | (2006.01) |
| *A61B 5/0205* | (2006.01) |
| *A61B 5/11* | (2006.01) |
| *H04M 3/56* | (2006.01) |
| *A61B 5/024* | (2006.01) |
| *A61B 5/021* | (2006.01) |

(52) U.S. Cl.
CPC ............. *H04W 4/22* (2013.01); *A61B 5/0205* (2013.01); *A61B 5/1117* (2013.01); *A61B 5/14532* (2013.01); *A61B 5/14542* (2013.01); *H04M 3/56* (2013.01); *A61B 5/021* (2013.01); *A61B 5/024* (2013.01)

(58) Field of Classification Search
CPC ............. H04W 68/00; G06Q 10/0833; G06K 2017/0045; G08B 13/2462; G08B 25/009; A61B 5/0022; A61B 5/02438; G06F 19/3418
See application file for complete search history.

(56) References Cited

U.S. PATENT DOCUMENTS

| | | | |
|---|---|---|---|
| 2005/0080322 A1* | 4/2005 | Korman | 600/300 |
| 2005/0206518 A1* | 9/2005 | Welch et al. | 340/539.12 |
| 2007/0042713 A1* | 2/2007 | Ayed | 455/41.2 |
| 2010/0295684 A1* | 11/2010 | Hsieh et al. | 340/573.1 |

* cited by examiner

*Primary Examiner* — Nizar Sivji
(74) *Attorney, Agent, or Firm* — Bell Nunnally & Martin LLP; Craig J. Cox

(57) ABSTRACT

The present disclosure provides for systems, devices, and methods which address needs of seniors, disabled persons, or any other similar users, at a stage in life when they can still live independently while benefiting from monitored care. Embodiments described herein enable a higher level of connectivity without requiring the member to be technologically savvy, and provides a simple mechanism for personalized emergency support. Embodiments utilize at least one personal communication device which may allow for remote interactions with medical and concierge personnel in a monitoring center or other emergency contacts, in order to fulfill requests for everyday needs, ranging from providing directions to a locations, to health alerts based on health and status measurements collected electronically and remotely.

20 Claims, 17 Drawing Sheets

SYSTEMS AND DEVICES FOR EMERGENCY TRACKING AND HEALTH MONITORING

CROSS REFERENCE TO RELATED INFORMATION

This application claims the benefit of U.S. patent application Ser. No. 12/614,242, now U.S. Pat. No. 8,942,676, filed Nov. 6, 2009, titled Systems and Devices for Emergency Tracking and Health Monitoring.

TECHNICAL FIELD

The present disclosure is directed to remote monitoring and communications devices. More specifically, the present disclosure is directed towards systems and methods for active monitoring, tracking, and emergency response, for users of a portable communications device from a central monitoring center.

BACKGROUND OF THE INVENTION

Many people are in a stage of life that whether due to age or disability or other conditions, they require some form of health, emergency monitoring, or other communication services while living independently. Unfortunately, many of these services offer limited connectivity and features, and therefore under serve the desires of their respective users. Further, devices which offer additional connectivity and features generally require more technological skill to operate than is feasible to expect from the users of these products.

Current monitoring and communications systems of this type are also generally restricted to being home-based systems. As a result, users of such systems are often left unprotected in the event that they want to go out and conduct every day activities. Another disadvantage of home-based designs is that even when in the home, a user-worn device generally communicates with an intermediate device which is tied to a home-based phone system, which are more prone to failure in power-loss and other emergency situations.

BRIEF SUMMARY OF THE INVENTION

The present invention is directed to a system and method which addresses needs of seniors, disabled persons, or any other users, at a stage in life when they can still live independently while benefiting from monitored care. Embodiments described herein enable a higher level of connectivity without requiring the member to be technologically savvy, and provides a simple mechanism for personalized emergency support. Moreover, embodiments may also allow for remote interactions with medical and concierge personnel, in order to fulfill requests for everyday needs, ranging from providing directions to a locations, to health alerts based on health measurements collected electronically and remotely.

Embodiments may utilize a companion device communicatively coupled to a cellular network. The companion device is preferably configured to establish voice and data communication with a monitoring center via the cellular network. Additionally, the companion device may be configured to allow for communication between a user and at least one other designated source, such as an emergency contact, via said cellular network. The companion device may be configured to measure, remotely obtain, and transmit health information, vital statistics, and other user emergency information.

Embodiments may utilize a personal user device communicatively coupled to the companion device. A personal device may be worn as a wrist device, necklace, or placed in any suitable manner according to desired functionality. Communication between the personal device and companion device may be implemented by any suitable protocol such as Blue Tooth, RF, Zigby, and the like. The user device is preferably configured to be disposed proximate to the user and may be further configured to actively monitor at least one user condition. The user device may report the monitored condition to said monitoring center through said companion device. The user device may be further configured to initiate or receive calls or alerts from any of the user device, companion device, or monitoring center.

A monitoring center, manned by medical and/or other professionals, will monitor and retain user medical statistics that are transmitted regularly, or on-demand, by devices available to users with specific needs. Such devices could be accelerometers (for fall detection), electronic scales, blood pressure cuffs, thermometers, blood sugar monitors, and many others; as such devices become available to market. These devices may be contained within the above-described user device, companion device, or both. These devices may also be implemented on a stand-alone basis and be placed in communication with a companion or personal user device. The measurements transmitted are automatically compared to individual profiles set for each user. A specialist alert is triggered when an abnormal reading is detected.

Embodiments may trigger alerts which correspond to personalized sequence of actions in the monitoring center, based on each user's medical profile, which could range from dispatching local medical help, contacting family, caregivers, or the users with alerts, medical recommendations and advice.

Other non-emergency services may also be provided either directly via the Internet or thru a phone call to the center. These services may include: account management, reporting on collected medical information, location services based on current GPS data, medical advice on common illnesses and conditions, setting up reminders and check-up calls, relaying messages to and from designated family or caregivers, e-mail, text messages, 3-way conferencing and others.

Based on cellular technology, all these services will be rendered without the need for the user to be restricted to the user's home, a medical facility, assisted home, or the like, thereby providing users with the independence to continue to live an active healthy life, while keeping family and caregivers confident that their well being is monitored.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
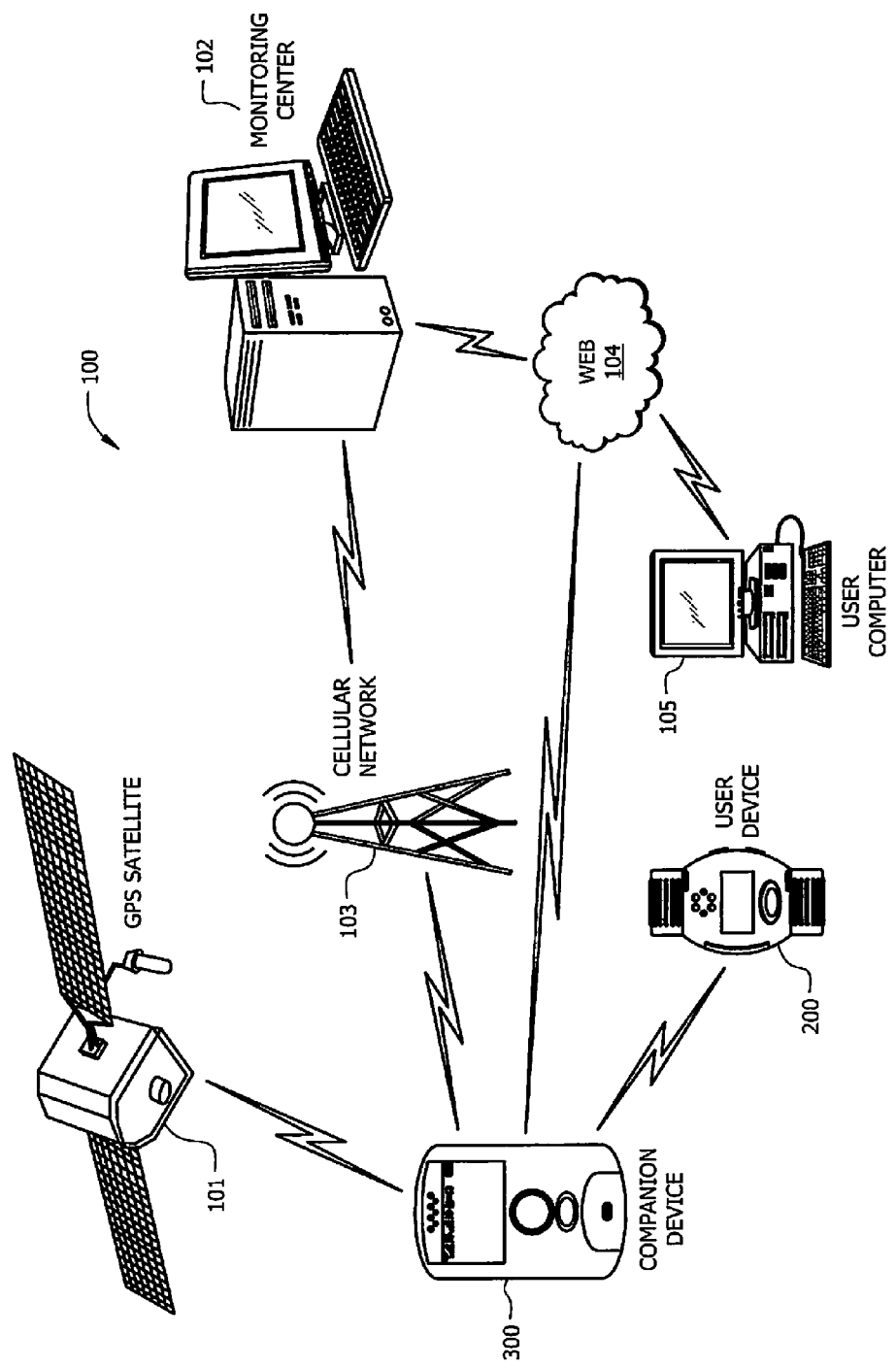
FIG. 1 illustrates an embodiment of an overall system in accordance to the present disclosure.

FIG. 1 illustrates an embodiment of an overall system 100 in accordance to the present disclosure. System 100 includes a companion device 300 which may be in communication with user device 200. A detailed discussion of companion device 300 and user device 200 is provided below with respect to FIGS. 2-3. Companion device 300 may receive a GPS signal from one or more GPS satellites 101 such that companion device 300 may know its location and may broadcast such location information to monitoring center 102 via cellular network 103 or web interface 104.

Cellular network 103 may be any type of communications network such as a GSM, CDMA, EDGE, WiMAX network, and the like. Cellular network 103 may also provide GPRS and SMS data services between companion device 300 and monitoring center 102. Companion device 300 may also be connected to monitoring center 102 through the web interface 104 via a home network, WiFi hotspot, or similar connection when such networks are accessible. Because companion device 103 is able to connect to such networks, a monitored user is not restricted to being within a particular area such as their home, and are more able to go out and accomplish every day tasks while still having the security of being monitored.

User computer 105 may be connected to monitoring center 102 via web interface 104. User computer may be utilized to provide profile information to monitoring center 102 for a user of companion device 300 and may be configured to obtain information from companion device.

Figure 2:
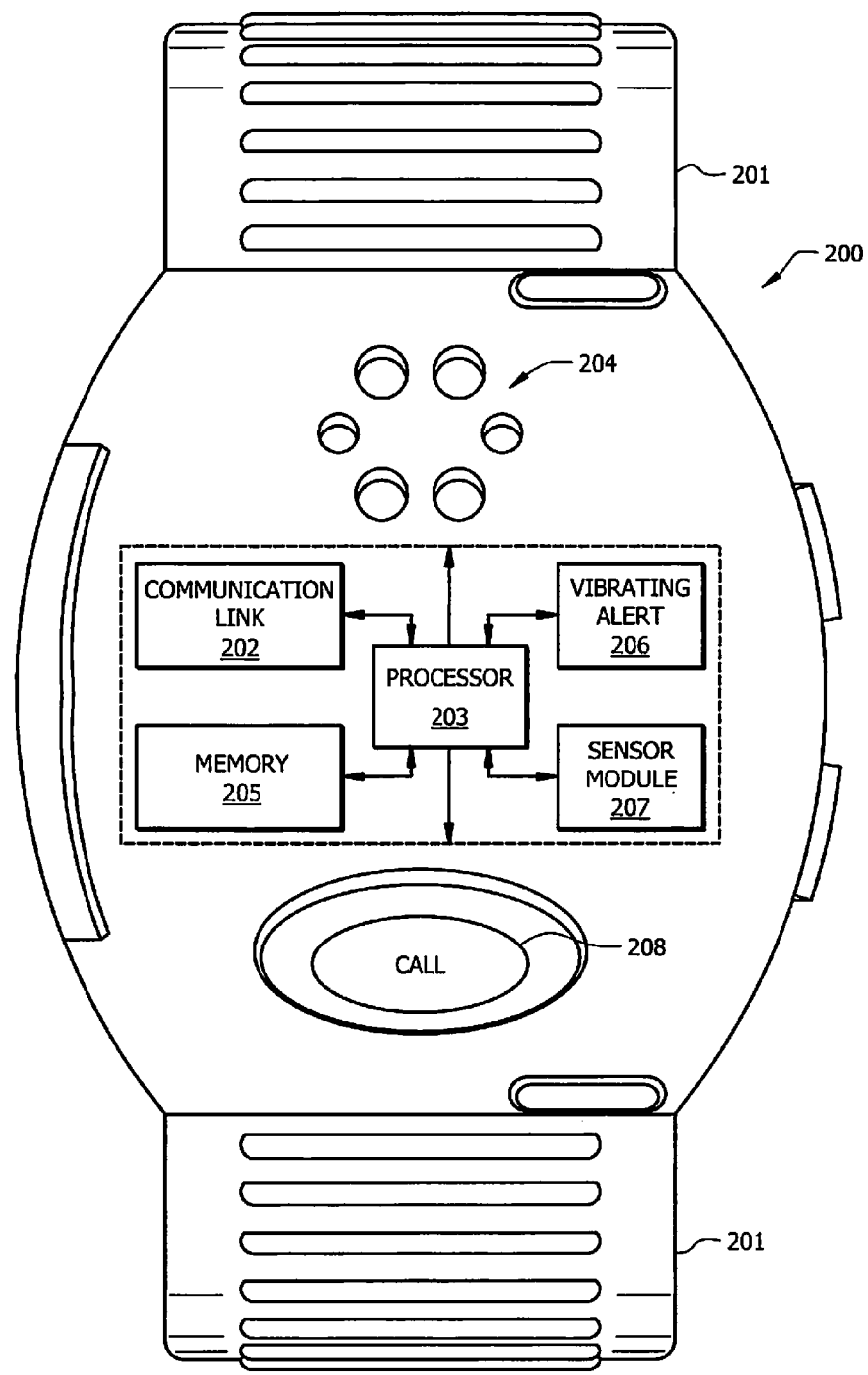
FIG. 2 illustrates an example embodiment of a personal user device in accordance with an exemplary embodiment of the present disclosure.

FIG. 2 illustrates an example embodiment of a personal user device 200 in accordance with an embodiment of the present disclosure. Personal user device 200 is designed to accompany a monitored user. The design of such a device may be such that it can be worn on by the monitored user, such as around the writs using wrist band 201. User device 200 is communicatively coupled to companion device 300 by any via communications link 202 which may utilize any suitable communication means (e.g., cordless phone protocols, Bluetooth, Zigby, and the like).

User device 200 may include processor 203 which controls various systems in user device 200. For example, processor 203 is connected to communications link 202 such that when a call is received over communications link 202, processor 203 may direct audio to output at speaker/microphone 204. Processor 203 may likewise direct audio obtained at speaker/microphone 204 to communications link 202 for transmission to companion device 300. Processor 203 may also monitor other systems of user device 200 and trigger alerts for a user. The types of alerts triggered can vary based on preferences of the type of system employed or based on preferences of the user. Alerts may include: an alarm when the communication like connection is disconnected due to long distance, an alarm to indicate low battery life on user device 200, a distress alarm when a user desires to draw attention to themselves, a fall alarm may be sent to monitoring center 102 upon sensing a monitored user has fallen, an emergency alarm sent to monitoring center 102, and the like. Such alerts could be audible and output through speaker 204, could be in the form of a vibrating alert using vibrating alert module 206, or could be silent and sent to monitoring center 102 which will respond accordingly.

In some embodiments a data transmission may be obtained over communications link 202. Such data transmissions could originate from monitoring center 102 for the purpose of activating or configuring user device 200. A configuration message may be stored to memory module 205. Data transmissions may also trigger pre-determined alters or notifications, and may function to activate portions of user device 200 such as to allow for the monitoring center 102 to talk to the monitored user using speaker/microphone 204.

Sensor module 207 may be provided to sense various aspects related to a monitored user. Sensor module 207 may be linked to devices on user device 200 which are configured to monitor health information such as pulse, blood pressure, blood sugar levels, blood-oxygen levels, etc. Sensor module 207 may also be equipped with accelerometers or other similar sensors which may sense when a monitored user falls or has a potentially harmful impact. In response to receiving data from sensor module 207, processor 203 may relay a data communication to communications link 202, which can then be delivered to the appropriate destination.

Call button 208 may be included on user device 200 to accept an incoming call, or to make an outgoing call. Call button 208 may be programmed to call monitoring center 102, or one of several other contacts to assist the monitored user. Processor 203 may be further configured to accept voice commands via speaker/microphone 204 upon activation of call button 208, and route communications to a requested destination.

Figure 3:
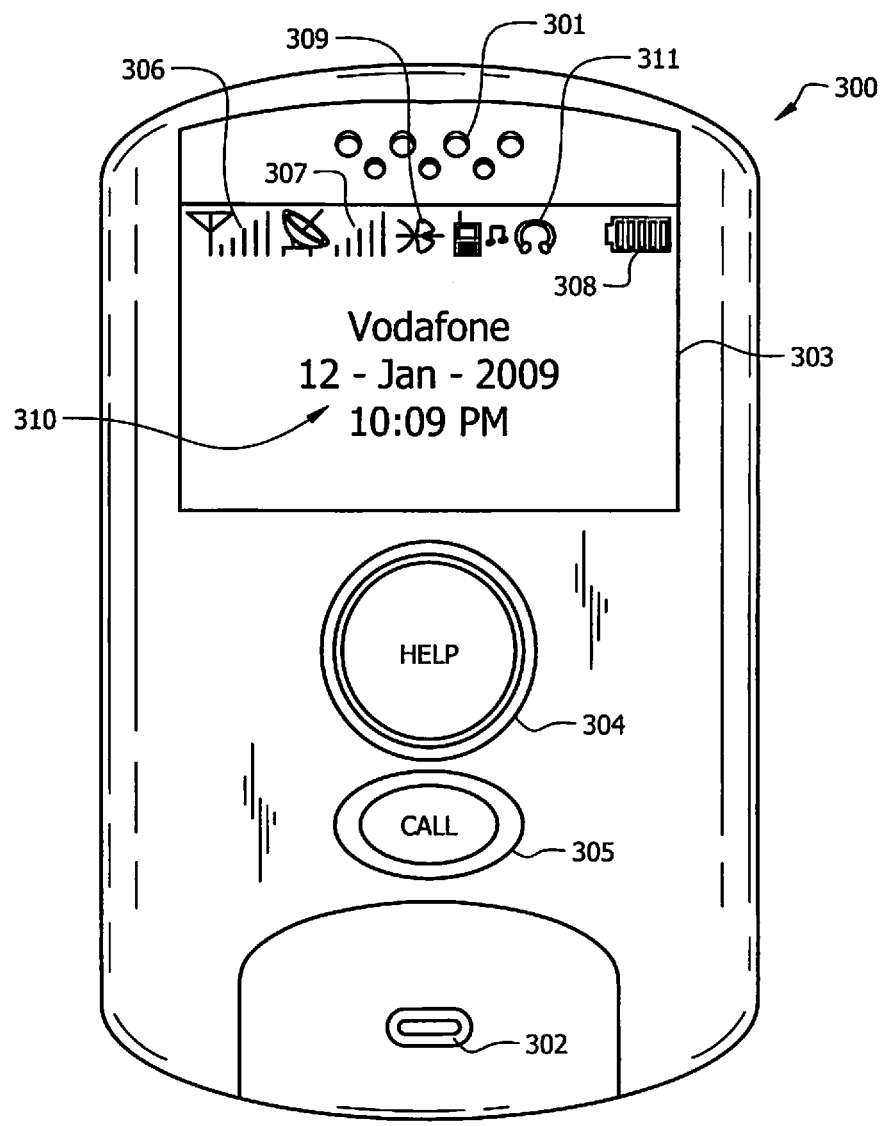
FIG. 3 illustrates an embodiment of a companion device in accordance with an exemplary embodiment of the present disclosure.

FIG. 3 illustrates an embodiment of a companion device 300 in accordance with an exemplary embodiment of the present disclosure. Companion device 300 may include a speaker 301, microphone 302, and display screen 303. The illustrated embodiment also includes a plurality of functional buttons 304 305, which may be pre-configured to execute desired functions. For example, companion device 300 includes a help button 304. When pressed by a monitored user, help button 304 may cause companion device 300 to contact monitoring center 102. An agent at monitoring center 102 may then interact with the monitored user via the speaker 301 and microphone 302. In the event that the agent receives no response, protocols may be implemented within the monitoring center that locate and the monitored user and send assistance to the location.

Companion device 300 further includes call button 305. When pressed, call button 305 may be configured to call one or more preselected numbers, and in some embodiments the user may select those numbers from a list or speak a voice command to dial a pre-designated number.

Display screen 303 may be included with companion device 300. Display screen 303 may include various signal strength indicators such as cellular network strength 306, and GPS network strength 307. Display screen 303 may also provide for a display of battery power indicator 308, Bluetooth connection indicator 309, date and time 310, and audio mode indicator 311. Because many times a monitored user will not necessarily be technologically adept, it may be preferable to display only items that are simple to understand.

It is further noted that companion device 300 may be configured to implement any of the functionality described with respect to user device 200, e.g., sensor module, alert, and communications functionality. Companion device 300 may also include additional capabilities such as an local area tracker which may indicate to a monitored user when they are leaving a specified service area. Companion device 300 may also be configured to trigger alerts when a user is experiencing low signal qualities, low battery, and the like.

Figure 4:
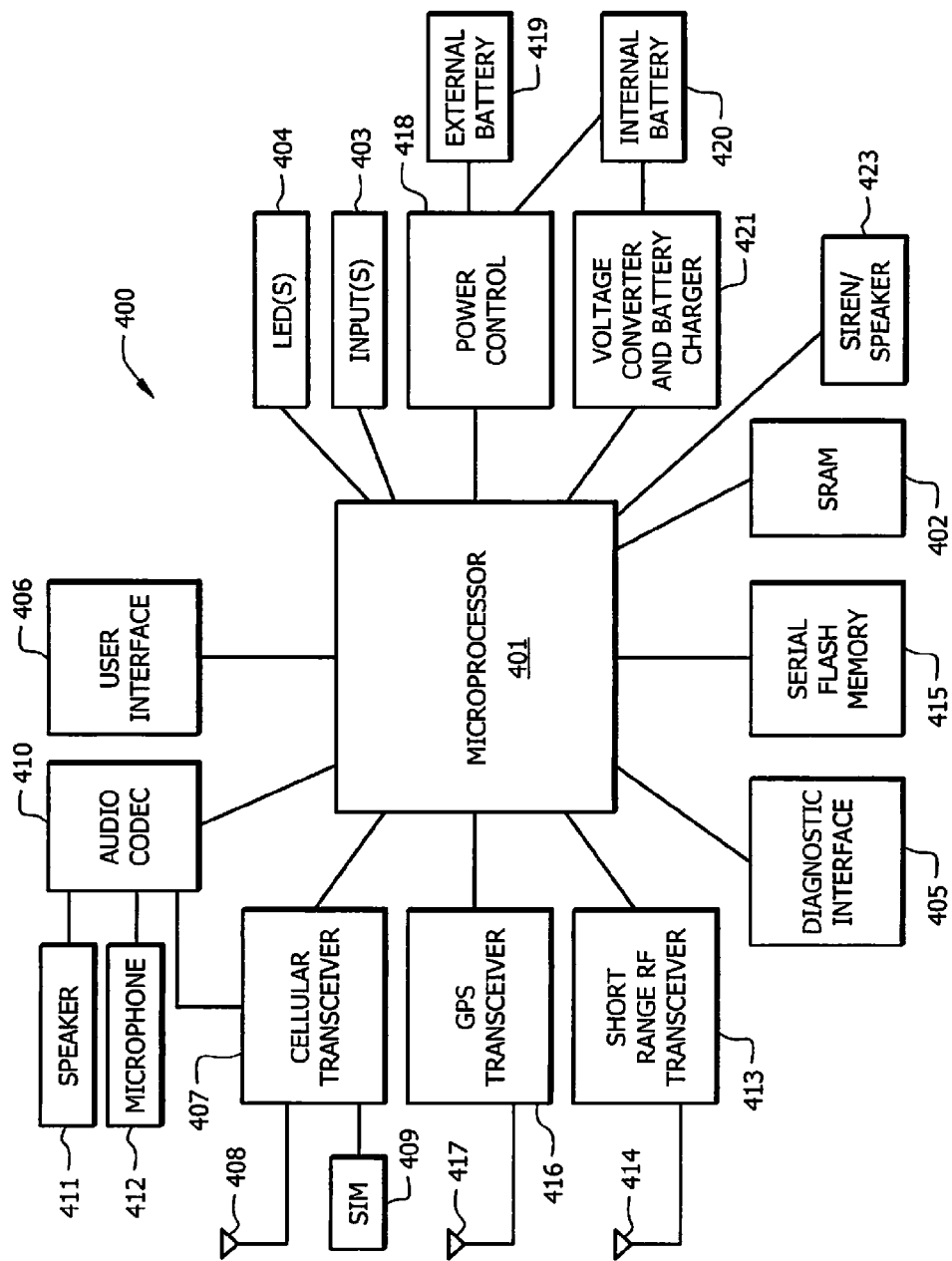
FIG. 4 is a functional block schematic implementing an embodiment of a companion device in accordance with an exemplary embodiment of the present disclosure.

Referring now to FIG. 4, an embodiment of the electronic aspects of companion device 300 is shown. The type of connection between the various components is a matter of design choice, and may vary depending upon the specific component chosen to perform for a particular function. Further, where a specific component is indicated, those skilled in the art will appreciate that the indicated component may be substituted with other, functionally equivalent components that are readily available in the marketplace.

Electronics 400 includes microprocessor 401. Microprocessor 401 controls overall operation of the device according to programming stored in memory 402, which can be SRAM memory. Electronics 400 may include inputs 403, which can be inputs such as switches or buttons, are included as inputs to microprocessor 401 and can be used to input data or provide for activation of pre-designated functionality controlled by microprocessor 401. In embodiments of the companion device, there is one button dedicated for activation of voice communications with the monitoring center. LEDs/Display 404 may be used to display function and status indicators. The programming stored in memory 402 may be placed there at the time of manufacture, and additional, new or modified programming may be uploaded to the device using a wired connection via the included diagnostic interface 405, user interface 406, or wirelessly via the cellular transceiver 407 received by antenna 408.

Cellular transceiver 407 may be of the GSM/GPRS variety, and may include a SIM card 409. Cellular transceiver 407 allows two-way voice and data communication between the remote device and the monitoring center 104 from FIG. 1. Voice communications are further enabled by a direct connection between cellular transceiver 407 and an audio codec 410, which encodes and decodes the digital audio signal portion of the wireless transmission, and an associated speaker 411 and microphone 412. Data communications preferably use the cellular data channel and/or the cellular control channel, which can make use of short message service (SMS) capabilities in the network. This has additional benefits in that it provides redundancy for cellular systems in which service for both types of data communication is supported. Also, for those cellular systems in which the voice channel cannot be used simultaneously with the data channel, or in which the data channel is simply unavailable, the control channel can provide a data link between the call center and the device.

Electronics 400 may also include short range wireless transceiver 413 and associated antenna 414, which, if included, allow for short range wireless voice and data communications with peripheral devices such as personal device 200. Wireless transceiver 413 may be designed and implemented using any wireless communication standards such as Bluetooth, 802.11 protocols, and the like, or any others which are known in the art. Microprocessor 401 can be programmed to pass through voice communications received by cellular transceiver 407 to a voice-capable peripheral when such a peripheral is employed when communications on the companion device and are activated. Voice communications received from a voice enabled peripheral, such as personal device 200, can be passed through to cellular transceiver 407 for transmission. Data generated by the device or received from a peripheral, if any, may be stored by microprocessor 401 in memory 415, which can be non-volatile memory such as serial flash memory until required by microprocessor 401 or until it is to be transmitted by the device.

GPS receiver 416 and antenna 417 receive signals transmitted by GPS satellites, the signal used to establish the geographical location of the device and the person being monitored. In one embodiment, data from GPS receiver 416 is passed through to microprocessor 401, which in turn processes the data to determine a location and associated time, and stores it in the serial flash memory 415 pending transmission using cellular transceiver 407. While electronics 400 are shown with a GPS receiver which passes the GPS signal data to the microprocessor for processing, a GPS engine which includes both the GPS receiver and the capability to process the GPS signal to produce a location determination and associated time indication may also be used according to the concepts described herein. Using a stand alone GPS engine would free processing bandwidth in the microprocessor, thereby allowing the microprocessor to perform other additional functions.

Cellular transceiver 407 may also be used to geographically locate the device through well known methods of cell tower triangulation, or may be used to provide location information used in assisted GPS schemes. Geographical location using cellular transceiver 407 may be performed in addition to, in conjunction with, or as a substitute for the GPS receiver 416. Other known methods for geographically locating the device may also be employed.

Either of memories 402 and 415, or memory resident on the microprocessor, may be used individually, or may be used in any combination to store the operating program and parameters for the operation of the device, as will be discussed later, and may further be used to store prerecorded messages which can be played through speaker 411 as part of the monitoring and alarm management system which may be utilized in response to various user situations. A siren/speaker 423 may also be included in the device and controlled by microprocessor 401. Siren 423 is also used as part of the alarm system and can be activated to provide an audible alarm. This alarm can be utilized to notify a user of a possible problem or to act as a panic alarm to warn those in the vicinity that the person being monitored may be in need of assistance, and can aid responders in the location of the person being monitored. The siren can be activated automatically by the microprocessor as part of the alarm management system or can be activated remotely by sending a signal to the microprocessor using cellular transceiver 407. Siren 423 can be a separate device or could be combined with the functionality of speaker 411.

In the embodiment shown in FIG. 4, power to the processor and other electronic components is provided though power controller 418 by external battery 419, or internal battery 420 when the external batter is disconnected or the voltage of the external battery falls below a threshold. External battery 419 is removable and is preferably rechargeable by a separate recharging unit. Also, the user will preferably have multiple external batteries so that a charged external battery can be immediately inserted when a discharged battery is removed. Internal battery 420 is preferably internal to the housing and not accessible by the person being monitored. The internal battery allows the device to continue to operate normally while the external battery is being replaced. As the internal battery is intended to supply power to the device only during the transitioning from a depleted external battery to a charged external battery, or to provide a short amount of time to acquire a charged battery, the internal battery does not need to have a large capacity. Internal battery 420 is charged using power from external battery 419 using voltage converter 421 and/or a battery charger which may be connected to the device through voltage converter 421.

Figure 5:
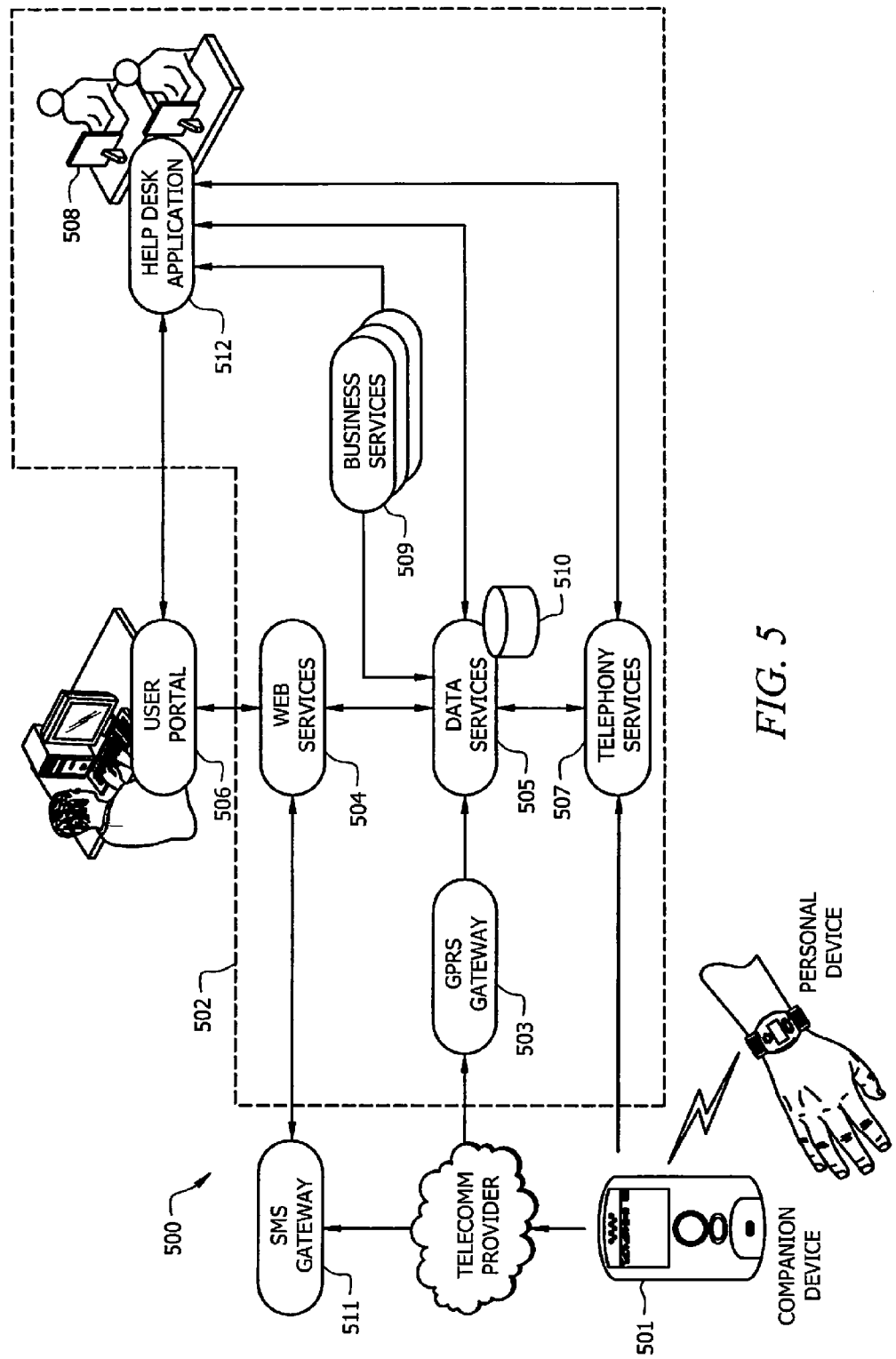
FIG. 5 illustrates a functional data flow diagram in accordance with an exemplary embodiment of the present disclosure.

FIG. 5 illustrates a functional data flow diagram of an embodiment of a system 500 as provided in the present disclosure. The first actor is the companion device 501 or device that initiates a call to the monitoring center 502. At the same time as the call, a data packet is sent with location information and conditions of the device.

The data packet is received by a [GPRS] gateway 503, that unwraps the 'envelope' of the message and calls the web services component 504 and 'post' the payload of the original message plus parameters associated to the message, such as timestamp, mobile originator, a message identifier and the gateway 503 that handled that packet. Web services component 504 will in turn store that message and its parameters on a table within data services block 505.

The same web services component 504 will provide a user portal 506 that allows members to access and update their information, and perform other member-oriented functions such as locating devices. In some embodiments, user portal 506 may be accessible to other authorized persons beside the user of device 501, to enable those persons to locate the user, update information on behalf of the user, and the like.

The voice call that was initiated by the user is received by the telephony services component 507, which routes it to help desk specialist 508 in standby. Telephony services component 507 also stores the call and routing information on data services block 505. Help desk application component 508 immediately loads the information and plots the location of that device and member, based on the call information that was stored on data services block 505 by telephony services component 507.

Business services component 509 runs in the background performing tasks that are independent of any actors initiation, such as message receiving, parsing, decoding and storage of monitoring information, monitoring alert thresholds, etc.

The system components discussed above may be implemented in many ways which will be apparent to those of skill in the art. Some example implementations are provided below:

Data services block 505 may include business database 510 where all data is stored and maintained. A simple implementation of business database 510 may use Microsoft SQL Server 2005 or 2008 Standard edition. MS SQL Server is a very efficient database server and it can be easily deployed either on the premises of monitoring center 502 or hosted by a 3rd party data provider. A logical design of the database may be implemented which includes generating tables, indexes, columns, relationships, etc. These elements will vary based on the data requirements, and the need for storing and maintaining data.

A message gateway can include GPRS gateway 503 and SMS gateway 511. The Message Gateway is a logical entity that can receive and process an IP message.

For GPRS messages GPRS Gateway 503 is preferably implemented as an on-premise Windows Service that encapsulates a socket application that can read a stream of bytes and interpret it as an individual message. The message itself is described by a data protocol and it is dependent on the device manufacturer. Messages from the same manufacturer will follow a single standard and will be self-describing based on message types and sub-types.

The message gateway will ordinarily be designed such that it is able to handle large volumes of messages. For that, in some embodiments it is preferable that the message gateway does not implement any business logic, but rather, limit itself to receiving, validating and storing the payload of the message. In such embodiments, business services component 509 is primarily responsible for the decoding of the payload and storing the contents of the message according to its categories and association with a specific account.

For receiving SMS messages, the most common and efficient method to implement an SMS gateway 511 is to contract a 3rd party provider that can abstract the intricacies of the operation and just provide us with the payload of the data message by calling an exposed web service, implemented on web services component 504.

In one embodiment, business services component 509 is a stand-alone service that implements business rules. Those rules could be from how to handle an incoming data packet, processing it, decoding it and storing it in the proper tables on the database, to thresholds on medical profiles and alerting, sending out automated text messages, or activating a help desk specialist if such thresholds are exceeded.

A typical implementation of business service component 509 is one or more Microsoft Windows Services that perform a specific function or a well defined set of functions. The advantage of such technology is that is perfectly integrated to the Windows Server Operating System, it can be installed, monitored and controlled (start, stop) using resources on the operating system making for a simple and easy implementation. The other advantage is that you can create multiple instances of such services allowing for horizontal scalability.

Those services can monitor a queue from Microsoft Message Queuing product, or lookup a database table for an incoming message, and take an action such as reading the message, translating it and storing into other specialized tables and at the same time associate.

In general, business service component 509 can be an instance of any business rule that needs to be performed on a regular basis, or based on a trigger, but independently of a human action. The complexity of business service component 509 will depend on the function it is designed to perform, e.g., the type of data that will be monitored for a user, automated actions to be taken, etc. The cost in this component is primarily on the development life cycle.

An embodiment of a help desk application 512 may be a Windows Forms (Desktop) application that allows help desk specialist 508 to interact with business services component 509, data service block 505, business database 510, and telephony system 507, and implement the mapping component of the application. Other possible alternatives are to develop the application as a web application hosted by the monitoring center's 502 web services component 504 or even leverage an existing help desk application 512 from a 3rd party company that already performs that kind of service and then 'plug-in' or extend their application.

Help desk application 512 preferably implements a dynamically-created script that takes in consideration specific member needs, medical conditions and personal selections. Help desk application 512 may load the most basic information about the caller so that the specialist can start handling the call knowing the caller name and other few basic information. The application 512 may also start loading the complementary information and plotting charts or maps.

The telephony service 507 infrastructure represents the set of services provided either on-premise or remotely that, as a basic service, has the ability to receive and route a call to a 'ready and able' help desk specialist 508. Other requirements for the telephony service 507 infrastructure are the ability to re-route calls in case no specialists are available to take calls, update the business database 510, either directly or indirectly, record calls, perform 3-way and conferencing and outbound calls, aside from automated dialing.

Embodiments of user portal 506 may be implemented as a web application that allows members or surrogates to subscribe to services, maintain information about themselves and execute a basic set of services such as locate device(s) on a map. The web application of user portal 506 may be hosted by web services component 504 and may have access to many aspects of the monitoring center infrastructure such as data services block 505, and business database 510, it may also provide access to a help desk specialist 508.

Examples of possible monitored user situations, and possible steps taken within the monitoring center and systems in general will be described below. It is noted that these examples are given for the purposes of illustrating the capabilities of the described devices, user portal, and monitoring center, and are not meant to be limiting in any manner. Many steps may be rearranged, combined, added to, or omitted based on preferences of a manufacturer, service provider, and/or user of embodiments of the present disclosure.

Case 1: Help Button Pressed by Monitored User

Figure 6:
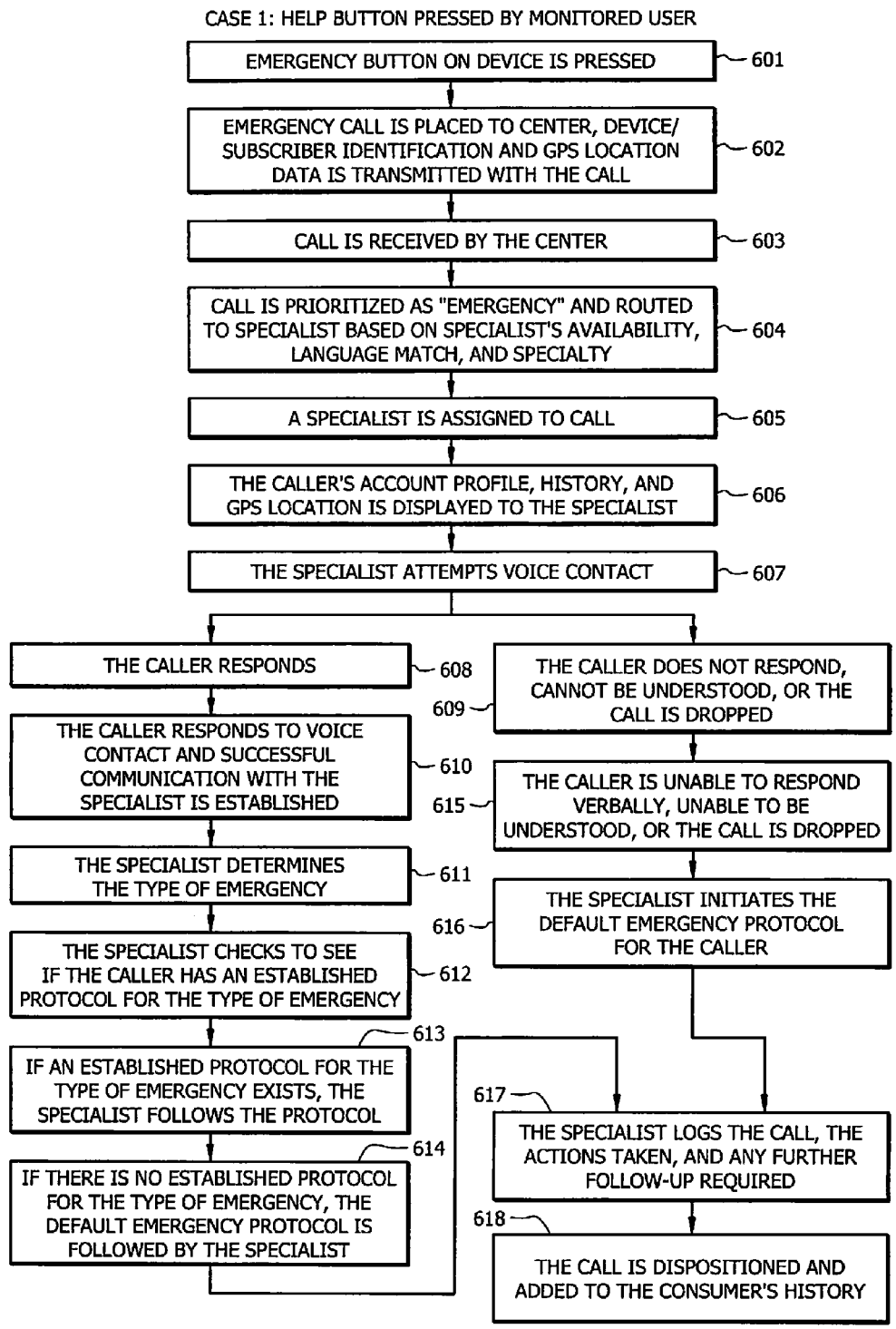
FIG. 6 illustrates a flowchart which outlines a method of handling a call transaction in accordance with an exemplary embodiment of the present disclosure.

FIG. 6 illustrates a flowchart in accordance with an embodiment of the present invention which outlines a possible method of handling a transaction where a help button is pressed by a monitored user. In block 601 an emergency button, such as help button 304 or call button 208 on a device, is pressed. An emergency call is placed to a monitoring center, such as monitoring center 502, and device/subscriber identification and GPS location data are transmitted with the call 602. The call is received by the monitoring center 603, is prioritized as an emergency, and routed to a specialist based on the specialist's availability, language match, specialty, and the like 604. A specialist 508 may then be assigned to the call 605. After the specialist 508 makes contact, the caller either responds 608, does not respond, cannot be understood, or the call is dropped 609.

In the event that the caller responds to voice contact, successful communication with specialist 508 is established 610. The specialist determines the type of emergency 611. In some circumstances the monitored user may have specific health concerns which are already known to and displayed to specialist 508 in monitoring center 502. The specialist may then check to see if the caller has an established protocol for the type of emergency 612. If an established protocol for the type of emergency exists, the specialist follows the protocol 613. If there is no established protocol for the type of emergency, a default emergency protocol may be followed by the specialist 614. Default emergency protocols may be user specific or based on a best practices approach for a monitoring center. Such protocols will vary and may be configured to account for many types of scenarios.

In the event that the caller is unable to respond verbally, unable to be understood, or the call is dropped 615, a specialist 508 may initiate a default emergency protocol for the caller 616. After the call is ended, a specialist may log the call, the actions taken, and may note any further follow-up that may be required 617. The call may then be dispositioned and added to the consumer's history 618.

Case 2: Fall Detection from Device

Figure 7:
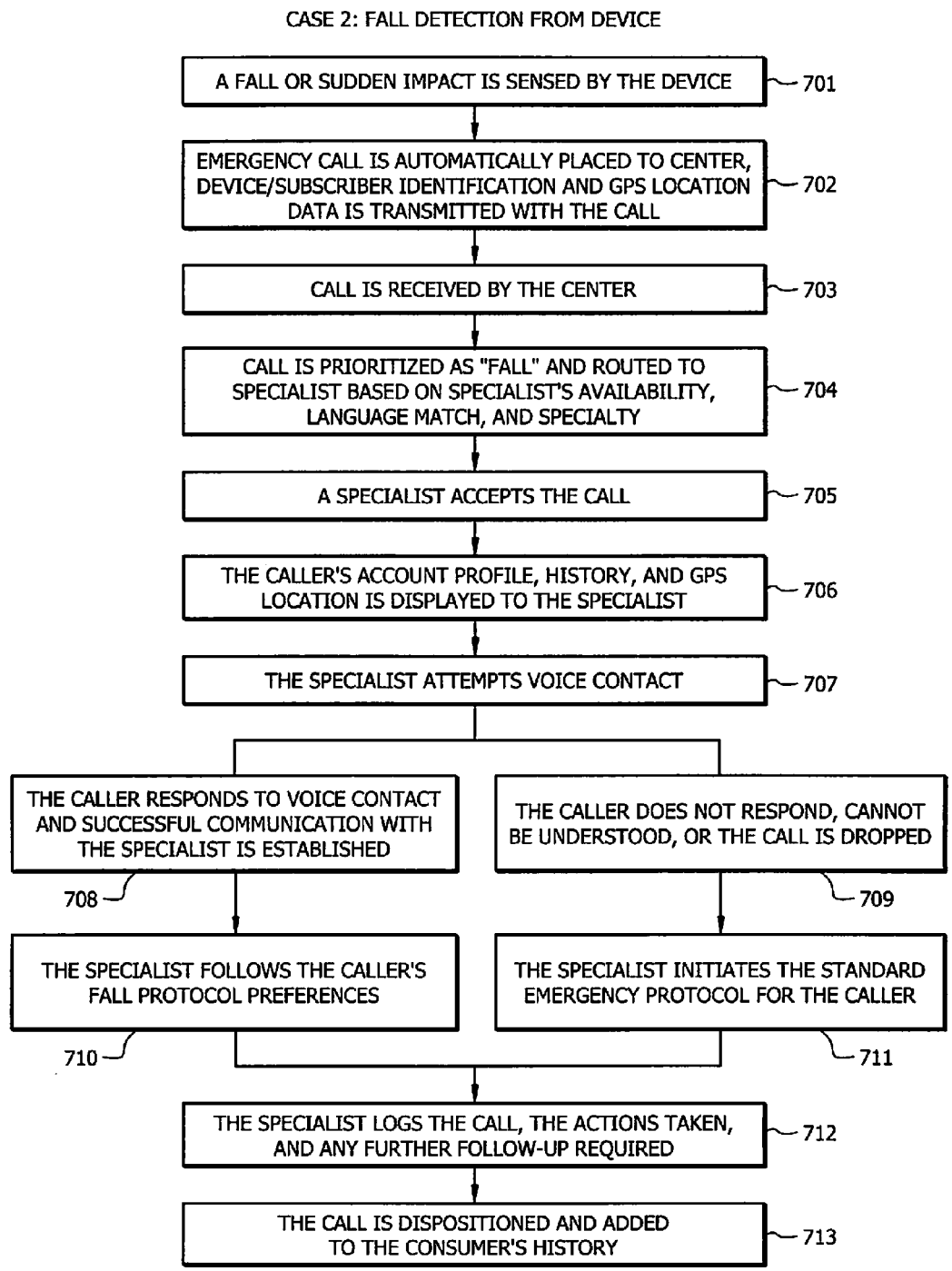
FIG. 7 illustrates a flowchart which outlines a method of handling a sensor detection transaction in accordance with an exemplary embodiment of the present disclosure.

FIG. 7 illustrates a flowchart in accordance with an embodiment of the present invention which outlines a possible method of handling a transaction where a fall detection is registered from a monitored user. This method may be used in conjunction with the systems and devices described above. In this scenario, a fall or sudden impact is sensed by the device 701. Such a fall may be sensed by sensor module 207 and may cause a device to initiate an emergency call to monitoring center 102. When an emergency call is automatically placed to center, the device/subscriber identification and GPS location data may be transmitted with the call 702. The call is then received by the center 703, is prioritized as a "fall," and routed to a specialist based on the specialist's availability, language match, specialty, and the like 704. After the specialist accepts the call 705, the caller's account profile, history, and GPS location may be displayed to the specialist 706.

The specialist may then attempt voice contact with the user 707. The user will either respond 708, will not respond, cannot be understood, or the call will have been dropped 709. In the event that the caller responds, successful communication with the specialist is established 708 and the specialist follows the user's fall protocol preferences 710. In the event that the caller is unable to respond verbally, unable to be understood, or the call is dropped 709, the specialist may initiate a standard emergency protocol for the caller 711.

After the situation is handled and the call transaction is completed, the specialist may log the call, document the actions taken, and note whether any further follow-up required 712. The call may then be dispositioned and added to the consumer's history 713.

Case 3: Route a Call to a "Ready" Help Desk

Figure 8:
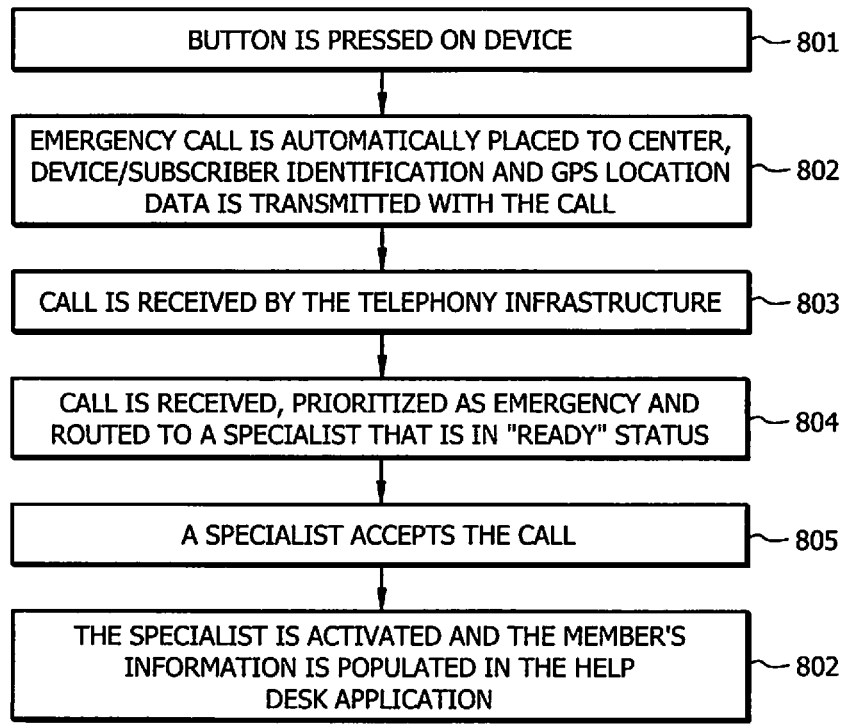
FIG. 8 illustrates a flowchart which outlines a method of routing an emergency call transaction in accordance with an exemplary embodiment of the present disclosure.

FIG. 8 illustrates a flowchart in accordance with an embodiment of the present invention which outlines a possible method of routing an incoming, user initiated, emergency call to a monitoring center. In the flowchart, a button, such as help button 304 or call button 208, is pressed on a device 801. An emergency call is automatically placed to center, and device/subscriber identification and GPS location data may transmitted with the call 802. The call is received by a telephony infrastructure 803, such as telephony services component 507, which is in communication with other portions of monitoring center 502. When the call is received, it may be prioritized as emergency and routed to a specialist, e.g., specialist 508, that is in 'Ready' status 804. A specialist accepts the call 805. The specialist is activated and the member's information is populated in a help desk application 806, such as Help Desk Application 512.

Case 4: Non-Emergency Call from Device to Monitoring Center

Figure 9A:
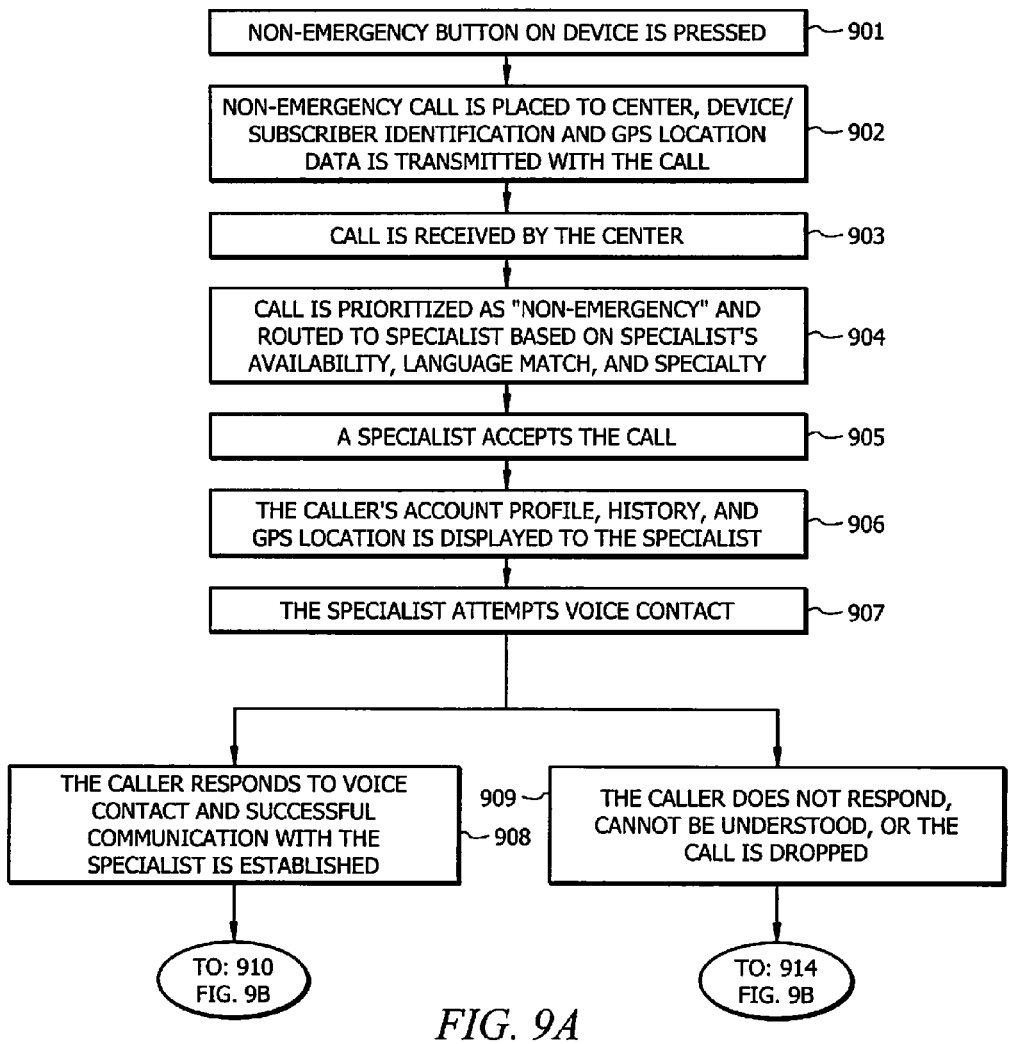
FIGS. 9A and 9B illustrate a flowchart which outlines a method of routing a non-emergency call transaction in accordance with an exemplary embodiment of the present disclosure.
Figure 9B:
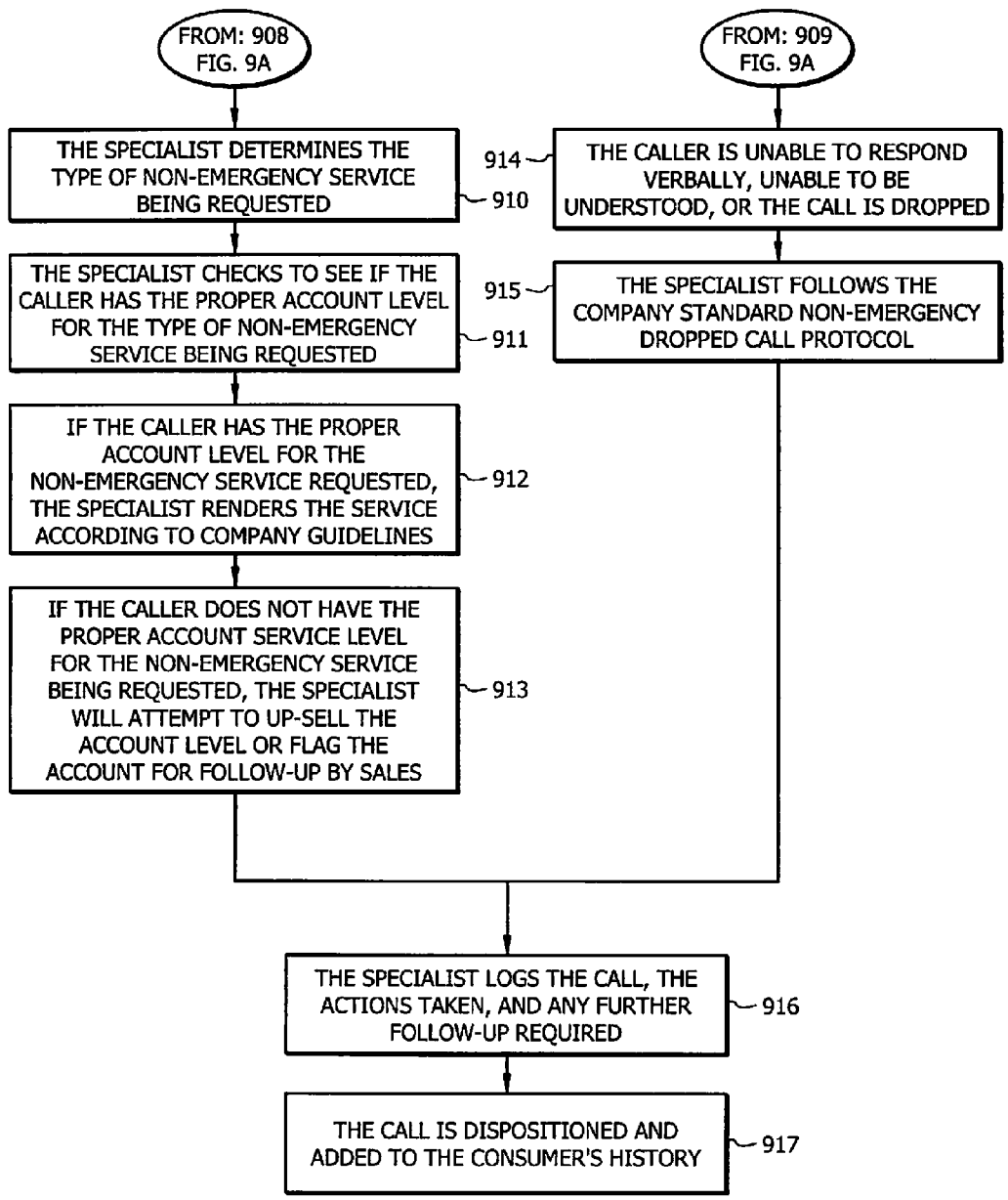

FIG. 9 illustrates a flowchart in accordance with an embodiment of the present invention which outlines a possible method of routing an incoming non-emergency call from a user to a monitoring center. In this flowchart, a non-emergency button, such as call button 305 or 208 on a device, is pressed 901. A non-emergency call is placed to center, and device/subscriber identification and GPS location data may be transmitted with the call 902. The call is received by the monitoring center 903 and is prioritized as a "non-emergency" call and is routed to a specialist based on the specialist's availability, language match, specialty, and the like 904.

A specialist accepts the call 905 and the user's account profile, history, and GPS location may be displayed to the specialist 906. This display may be made via Help Desk Application 508 discussed above, in combination with other elements of monitoring center 502. The specialist may then attempt voice contact 907. In the event that the caller responds to voice contact, successful communication with the specialist is established 908 and the specialist determines the type of non-emergency service being requested 910. The specialist may check to see if the caller has the proper account level for the type of non-emergency service being requested 911. If the caller has the proper account level for the non-emergency service requested, the specialist renders the service according to company guidelines 912. If the caller does not have the proper account service level for the non-emergency service being requested, the specialist may attempt to up-sell the account level or flag the account for follow-up by sales staff 913.

In the event that the caller is unable to respond verbally, unable to be understood, or the call is dropped 909, the specialist may follow a company standard non-emergency dropped call protocol 915.

After a non-emergency call, the specialist may log the call, document the actions taken, and note any further follow-up actions that may be required 916. The call may also then be dispositioned and added to the consumer's history 917.

Case 5: Display User Information to Help-Desk Specialist

Figure 10:
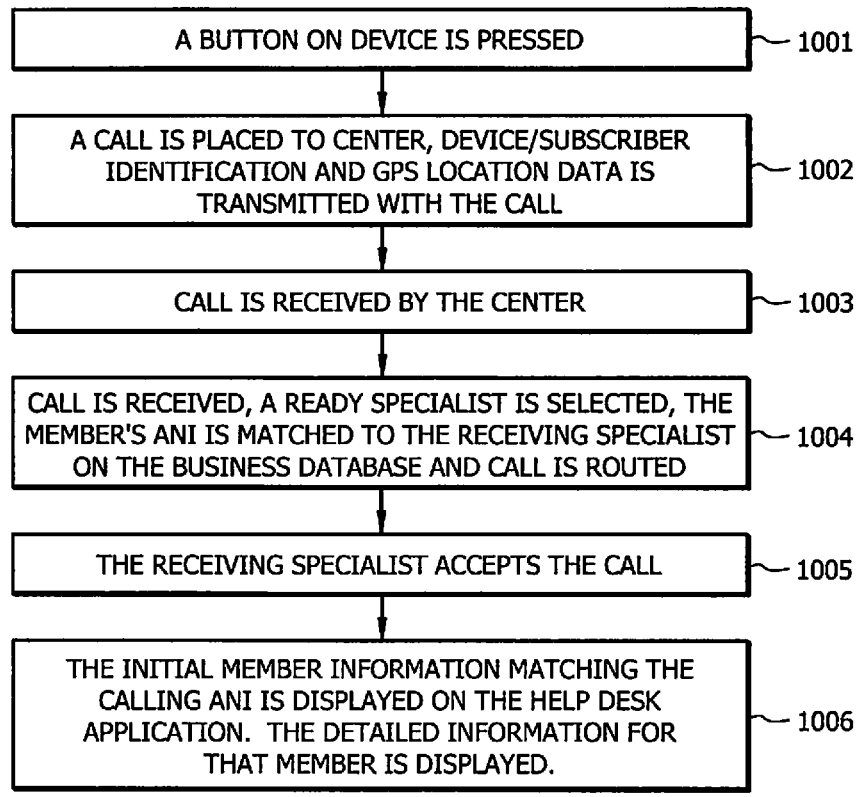
FIG. 10 illustrates a flowchart which outlines a method of displaying user information at a monitoring center in accordance with an exemplary embodiment of the present disclosure.

FIG. 10 illustrates a flowchart in accordance with an embodiment of the present invention which outlines a possible method of displaying user information to a help-desk specialist in a monitoring center. For example, when a button on device is pressed 1001, a call is placed to the monitoring center, and device/subscriber identification and GPS location data may be transmitted with the call 1002. When the call is received by the monitoring center 1003, a ready specialist may be selected. The member's telephone number is detected by Automatic Number Identification ("ANI") and may be matched to the receiving specialist on the Business Database, and the call is routed 1004. The receiving specialist accepts the call 1005. The initial member information matching the calling ANI is displayed on the Help Desk Application and detailed information for that member is displayed 1006.

Case 6: Map User's Last Location

Figure 11:
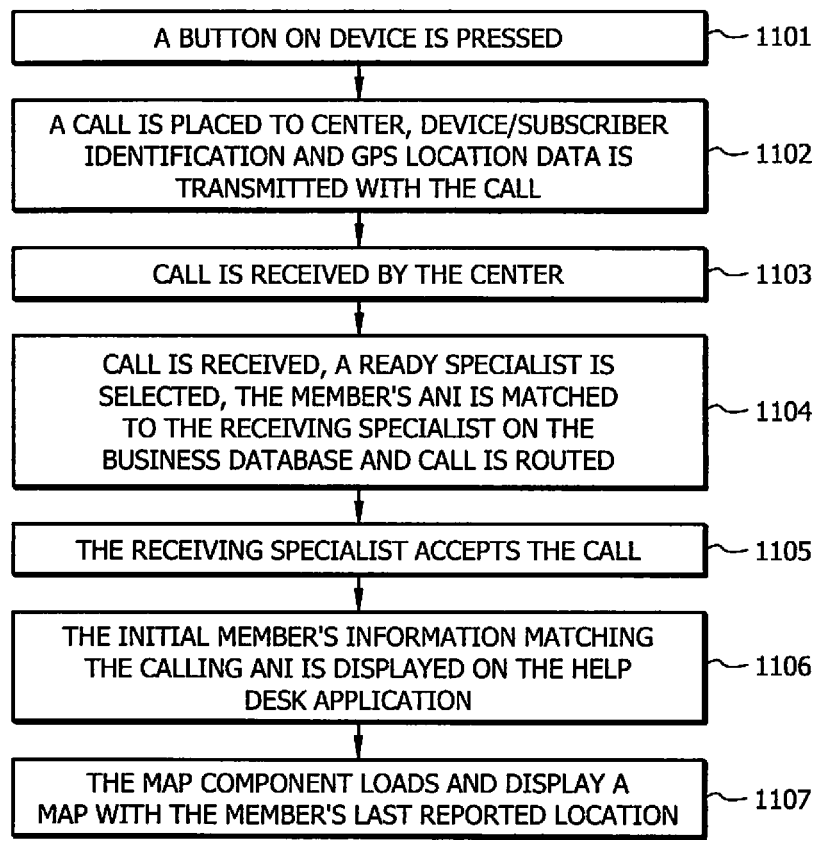
FIG. 11 illustrates a flowchart which outlines a method of mapping a user's location in accordance with an exemplary embodiment of the present disclosure.

FIG. 11 illustrates a flowchart in accordance with an embodiment of the present invention which outlines a possible method of mapping a user's last known location for use at a monitoring center. When a button on a device is pressed 1101 a call is placed to center, and device/subscriber identification and GPS location data may transmitted with the call 1102. The call is received by the monitoring center 1103, a ready specialist is selected, the user's ANI may be matched to the receiving specialist on the Business Database and the call is routed 1104. The receiving specialist accepts the call 1105. The initial user's information matching the calling ANI may be automatically displayed on the Help Desk Application 1106 and a map component may load and display a map with the user's last reported location 1107. This information may then be used by the specialist to provide a number of services, including giving directions to a user, or directing a third party to a user's location.

Case 7: Track User Location History

Figure 12:
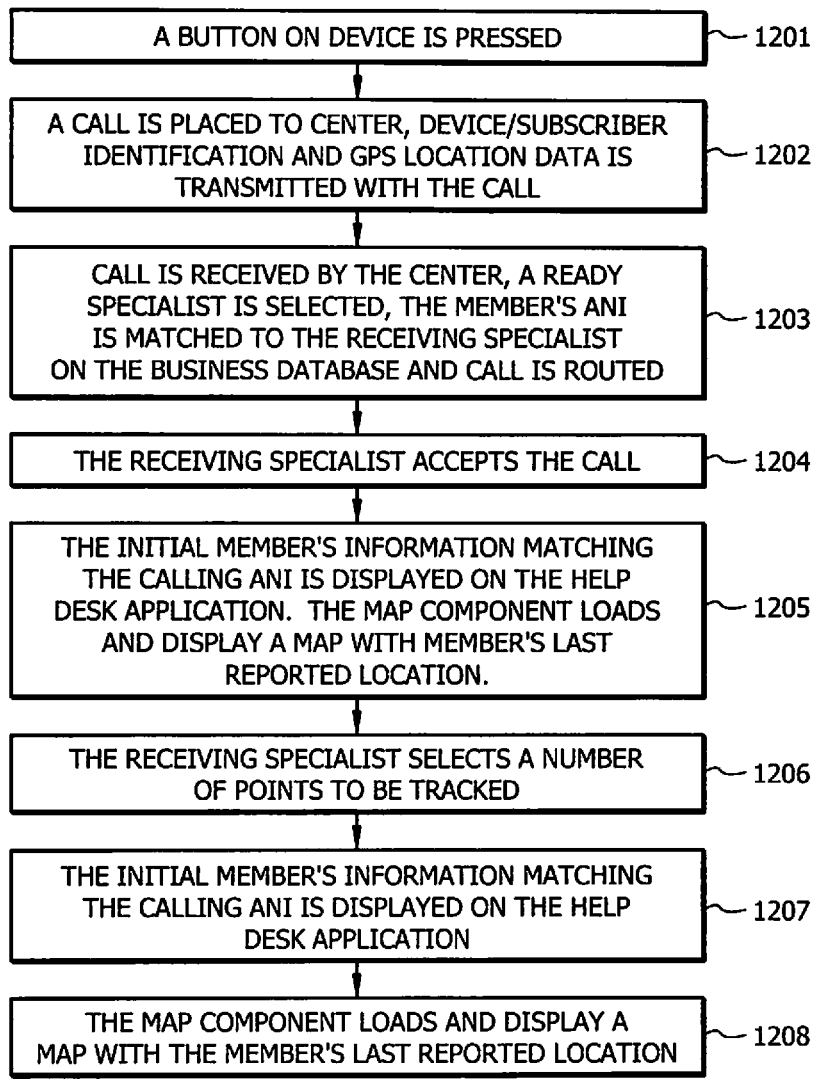
FIG. 12 illustrates a flowchart which outlines a method of tracking a user's location history in accordance with an exemplary embodiment of the present disclosure.

FIG. 12 illustrates a flowchart in accordance with an embodiment of the present invention which outlines a possible method of tracking a user's location history. Similar to case 6 above, when a button on device is pressed 1201, a call is placed to center, and device/subscriber identification and GPS location data may be transmitted with the call 1202. The call is received by the monitoring center and a ready specialist is selected. The user's ANI may be matched to the receiving specialist on the Business Database and the call is routed 1203. The receiving specialist accepts the call 1204. The initial user's information matching the calling ANI may be automatically displayed on the Help Desk Application and a map component may load and display a map with the member's last reported location 1205. The receiving specialist may select one or more points to be tracked 1206. The initial member's information matching the calling ANI may be displayed on the Help Desk Application 1207, and a map component may load and display a map with the member's last reported location(s) 1208. As with case 6 shown above, this information may then be used by the specialist to provide a number of services, including giving directions to a user, or directing a third party to a user's last known location, or toward a last known path traveled by a user.

Case 8: Find Primary/Secondary Emergency Contacts for User

Figure 13:
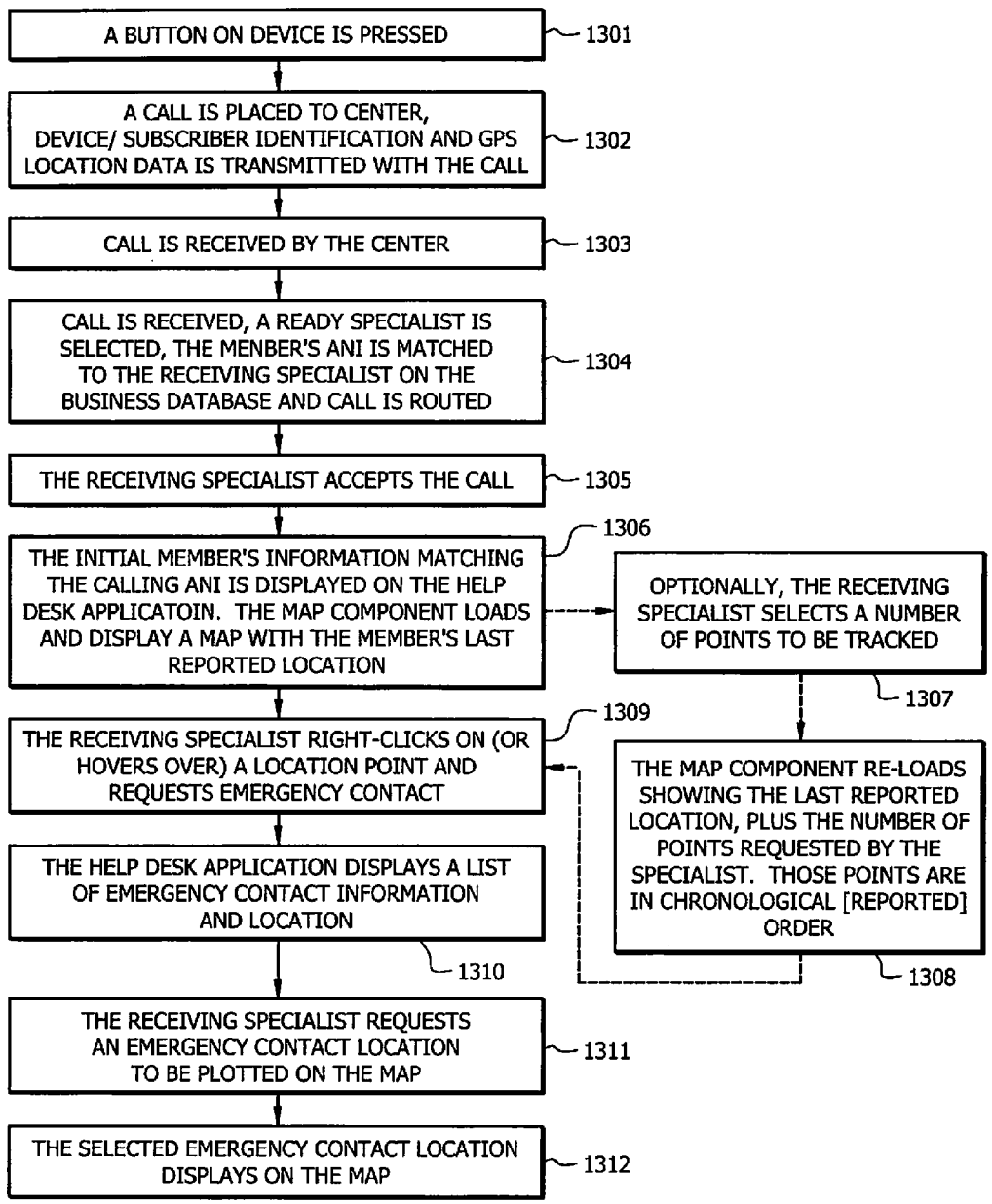
FIG. 13 illustrates a flowchart which outlines a method of finding a primary or secondary contact for a user in accordance with an exemplary embodiment of the present disclosure.

FIG. 13 illustrates a flowchart in accordance with an embodiment of the present invention which outlines a possible method finding a primary or secondary emergency contact for a user in the context of a user event. An emergency contact may include a family member/guardian, medical personnel, or any other person that a user may desire to contact. Such contacts may be pre-determined, or stated in the context of a user-initiated call.

In this method a button on device is pressed 1301 which causes a call to be placed to center. The device/subscriber identification and GPS location data may be transmitted with the call 1302. When the call is received by the center 1303, a ready specialist may be selected, the user's ANI may be matched to the receiving specialist on the Business Database, and the call is routed 1304. The receiving specialist accepts the call 1305 and the initial member's information matching the calling ANI may be automatically displayed on the Help Desk Application, and the map component may load and display a map with the user's last reported location 1306.

Optionally, the receiving specialist may select a number of points to be tracked 1307. In this case, the map component may re-load to show the last reported location, and/or the number of points requested by the specialist and those points are in chronological [reported] order 1308. The receiving specialist may select, e.g., by right-clicking or hovering over, a location point and request an emergency contact 1309. The Help Desk application displays a list of emergency contact information and locations 1310. Optionally the receiving specialist may request an emergency contact's location to be plotted on the map 1311. The selected emergency contact's location may then be displayed on the map 1312.

Case 9: Specialist Call Out and Conference in Emergency Services

Figure 14:
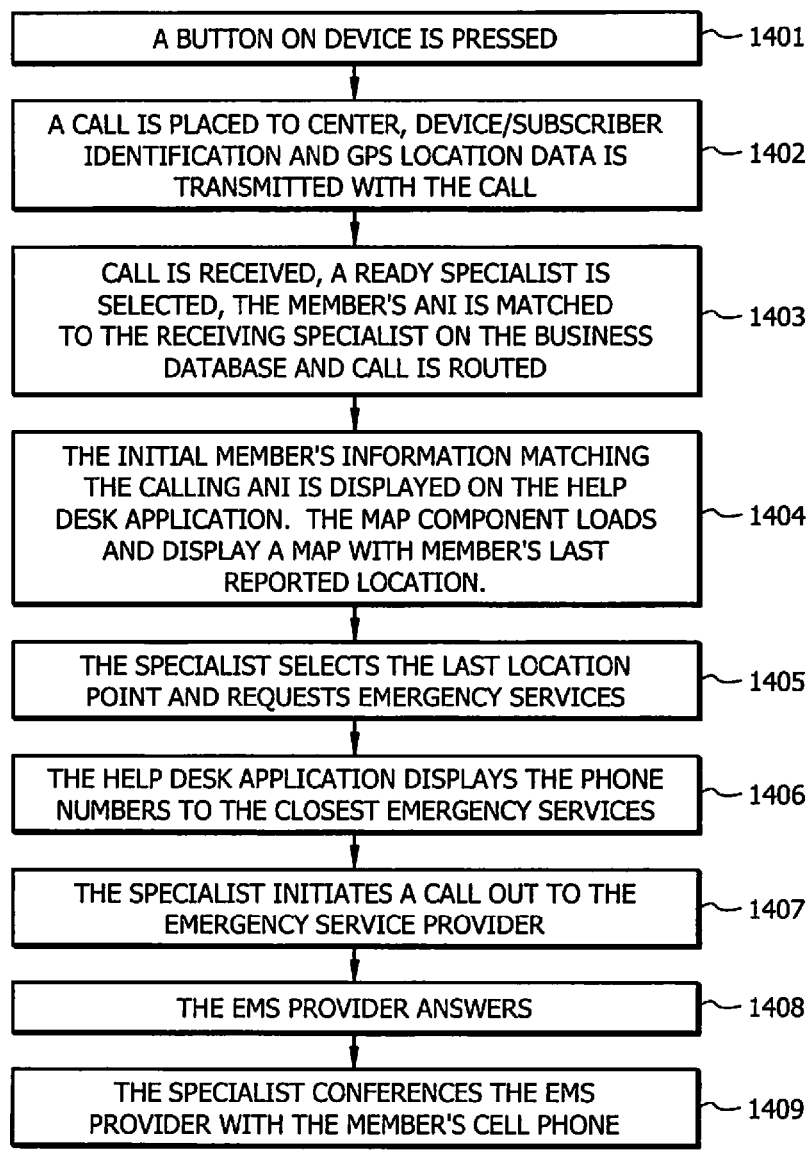
FIG. 14 illustrates a flowchart which outlines a method of contacting emergency services personnel in accordance with an exemplary embodiment of the present disclosure.

FIG. 14 illustrates a flowchart in accordance with an embodiment of the present invention which outlines a possible method for a monitoring center specialist to communicate with an emergency services contact in the context of a user event. When a button on device is pressed 1401, a call is placed to center. The device/subscriber identification and GPS location data may be transmitted with the call 1402. The call is received by the center, a ready specialist is selected, the user's ANI may be matched to the receiving specialist on the Business Database, and the call is routed 1403. The initial user's information matching the calling ANI may be displayed on the Help Desk Application and the map component may load and display a map with the user's last reported location 1404. The specialist may then select the last location point and requests emergency services 1405. The Help Desk Application displays the phone numbers to the closest emergency services 1406. The specialist initiates a call out to the emergency service provider 1407. After the EMS provider answers 1408, the specialist may conference the EMS provider with the member's cell phone 1409.

Cases 10-11: Access to User's Portal for Information Update and Services

Figure 15:
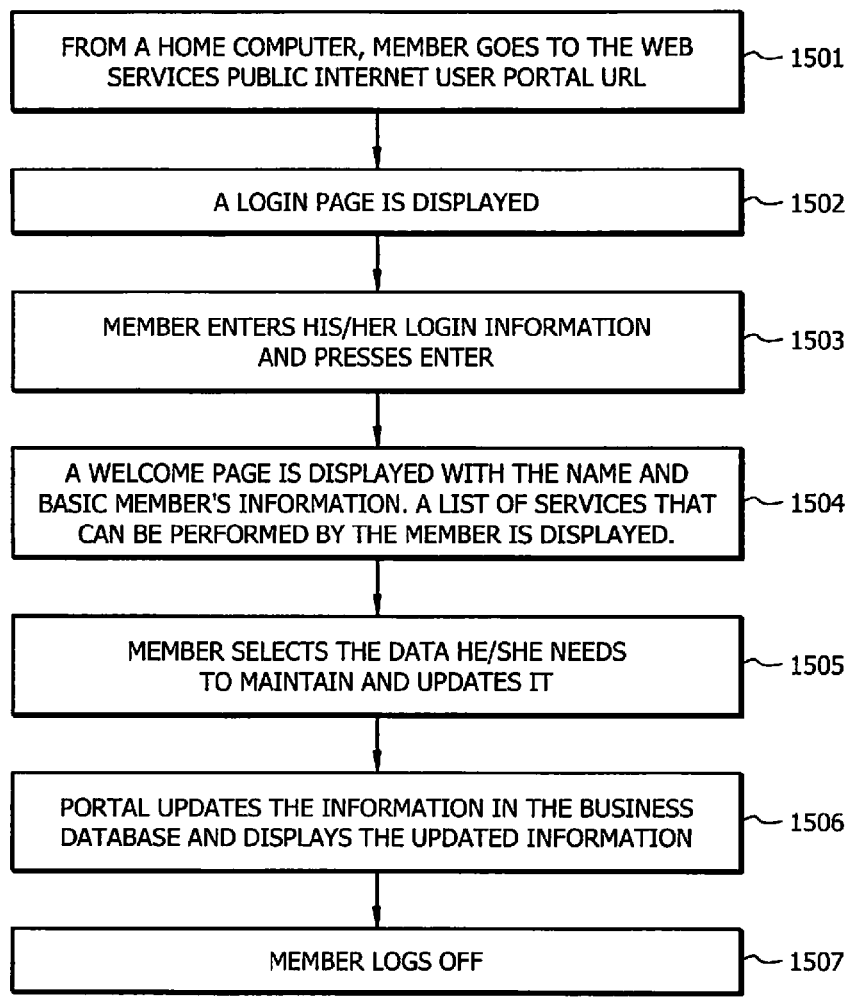
FIG. 15 illustrates a flowchart which outlines a method of accessing a user portal in accordance with an exemplary embodiment of the present disclosure.
Figure 16:
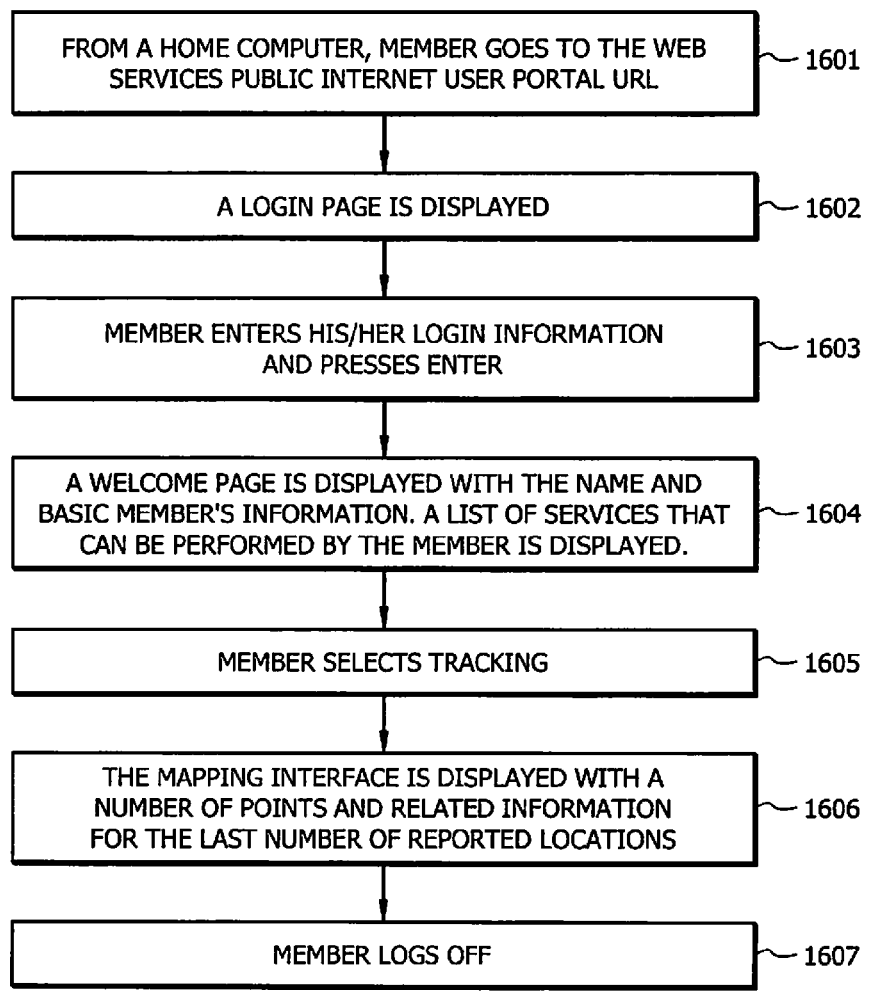
FIG. 16 illustrates a flowchart which outlines a method of accessing a user portal in accordance with an exemplary embodiment of the present disclosure.

FIGS. 15-16 illustrate flowcharts in accordance with embodiments of the present invention which outlines possible methods for accessing a user portal for obtaining information, adding services, updating user information, and the like. As stated above, an authorized user may utilize the portal for many reasons including account maintenance, profile/service updates, etc.

From a computer, member may navigate to the web services public internet user portal URL 1501 1601, this portal may be user portal 506 as described above. A login page may be displayed 1502 1602, wherein a user enters his/her login information and hit enter 1503 1603. Initially, it may be preferred to display a welcome page with a name, basic user information, and a list of services that can be performed by the user 1504, 1604. The user may select the data he/she needs to maintain and updates it 1505. After selections are made, the portal may update the information in the Business Database and display the updated information 1506. The portal application may also be utilized by a user to track a monitored user. After logging on, a user may select a tracking option 1605. The mapping interface may be displayed with a number of points and related information for the last number of reported locations 1606. This feature may assist a family member or guardian in tracking a monitored user in the event that the monitored user may be lost or unavailable. When a portal session is completed, a user may log off 1507 1607, or the session may be automatically terminated.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for administering system for monitoring users of said system, said method comprising:
    connecting a monitoring center to a plurality of companion devices over a cellular network, said plurality of companion devices configured to provide information corresponding to users of said plurality of companion devices to said monitoring center;
    receiving, from one of the plurality of companion devices, a trigger event that requires attention from the monitoring center;
    retrieving user information for the user of the one of the plurality of companion devices;
    retrieving status information, and location information for the user of the one of the plurality of companion devices; and
    determining a preferred emergency contact for the user of the one of the plurality of companion devices from a list of emergencies contacts based on a relative location of each emergency contact from the list of emergency contacts to a current location of the user of the one of the plurality of companion devices;
    wherein the monitoring center includes a helpdesk center application in communication with a data service application and a telephone application; and
    wherein the trigger event is reported to the helpdesk application by the data service application and a two way voice communication is established with the help desk application using the telephone application.

2. The method of claim 1 wherein the trigger event is a pressing of a call button by the user of the one of the plurality of companion devices.

3. The method of claim 1 wherein the pressing of a call button by the user is an emergency call button.

4. The method of claim 1 wherein the trigger event is an alert from the one of the plurality of companion devices, the alert occurring when a monitored health condition is outside of a predetermined acceptable range.

5. The method of claim 1 wherein the trigger event is an alert from the one of the plurality of companion devices, the alert occurring when a fall is detected by the one of the plurality of companion devices.

6. The method of claim 1 wherein, in addition to the companion device, the user has a user device communicatively coupled to the companion device.

7. The method of claim 6 wherein said user device includes at least one sensor measuring biometric data for the user.

8. The method of claim 6 wherein the user device includes an emergency button.

9. The method of claim 6 wherein user device is in the form of a watch.

10. The method of claim 1 wherein the companion device is a cellular phone.

11. A method for administering system for monitoring users of said system, said method comprising:
- connecting a monitoring center to a plurality of companion devices over a cellular network, said plurality of companion devices configured to provide information corresponding to users of said plurality of companion devices to said monitoring center;
- receiving, from one of the plurality of companion devices, a trigger event that requires attention from the monitoring center;
- retrieving user information for the user of the one of the plurality of companion devices;
- retrieving health status information, and location information for the user of the one of the plurality of companion devices;
- initiating, by the monitoring center, a voice call with an emergency service provider;
- establishing a three-way voice conference call between the monitoring center, the emergency service provider and the user of the one of the plurality of companion devices using the one of the plurality of companion devices;
- wherein the monitoring center includes a helpdesk center application in communication with a data service application and a telephone application; and
- wherein the trigger event is reported to the helpdesk application by the data service application and a two way voice communication is established with the help desk application using the telephone application.

12. The method of claim 11 wherein the trigger event is a pressing of a call button by the user of the one of the plurality of companion devices.

13. The method of claim 11 wherein the pressing of a call button by the user is an emergency call button.

14. The method of claim 11 wherein the trigger event is an alert from the one of the plurality of companion devices, the alert occurring when a monitored health condition is outside of a predetermined acceptable range.

15. The method of claim 11 wherein the trigger event is an alert from the one of the plurality of companion devices, the alert occurring when a fall is detected by the one of the plurality of companion devices.

16. The method of claim 11 wherein, in addition to the companion device, the user has a user device communicatively coupled to the companion device.

17. The method of claim 11 wherein said user device includes at least one sensor measuring biometric data for the user.

18. The method of claim 17 wherein the user device includes an emergency button.

19. The method of claim 17 wherein user device is in the form of a watch.

20. The method of claim 11 wherein the companion device is a cellular phone.

\* \* \* \* \*